United States Patent
Nagasawa et al.

(10) Patent No.: US 6,900,037 B2
(45) Date of Patent: May 31, 2005

(54) METHOD FOR PRODUCING AMIDE COMPOUNDS

(75) Inventors: Tohru Nagasawa, Gifu (JP); Akinobu Matsuyama, Tsukuba (JP)

(73) Assignee: Daicel Chemical Industries, Ltd., Osaka (JP)

( * ) Notice: Subject to any disclaimer, the term of this patent is extended or adjusted under 35 U.S.C. 154(b) by 20 days.

(21) Appl. No.: 10/172,569

(22) Filed: Jun. 13, 2002

(65) Prior Publication Data

US 2003/0124691 A1 Jul. 3, 2003

(30) Foreign Application Priority Data

Jun. 15, 2001 (JP) ......................................... 2001-182545

(51) Int. Cl.$^7$ ............................ C12P 13/02; C12P 7/40; C12P 41/00
(52) U.S. Cl. ....................................... 435/129; 435/280
(58) Field of Search ............................. 435/129, 252.3, 435/280; 45/280

(56) References Cited

U.S. PATENT DOCUMENTS

| 5,258,305 A | * | 11/1993 | Yamada et al. ............. 435/280 |
| 5,866,379 A | | 2/1999 | Burlingame et al. ......... 435/129 |

FOREIGN PATENT DOCUMENTS

| CN | 1290296 T | 4/2001 |
| EP | 1055724 A1 | 11/2000 |
| JP | 4-222591 | 8/1992 |
| JP | 8-089267 | 4/1996 |
| JP | 11-123098 | 5/1999 |
| JP | 2000-175681 A | 6/2000 |
| JP | 2002-325587 A | 11/2002 |
| WO | WO 98/32872 A1 | 7/1998 |
| WO | WO 00/36086 A1 | 6/2000 |
| WO | WO 02/07017 A3 | 9/2002 |
| WO | WO 02/07017 A2 | 9/2002 |
| WO | WO 02/070717 A2 | 9/2002 |

OTHER PUBLICATIONS

Okano, V. et al. "Kinetic secondary deuterium isotope effects for substituted benzaldehyde cyanohydrin formation," *J. Am. Chem. Soc.* 98(14):4201–4203 (Jul. 7, 1976).

Cramp Ra et al. Molecular characterisation of a novel themophilic nitrile hydratase. Biochim Biophys Acta. Apr. 12, 1999;1431(1):249–60.

Ingvoren, K et al. Microbial hydrolysis of organic nitriles and amides. Ciba Found Symp. 1988;140:16–31.

Prepechalova, I et al. Purification and characterization of the enantioselective nitrile hydratase from Rhodococcus equi A4. Appl Microbiol Biotechnol. Mar. 2001;55(2):150–6.

* cited by examiner

*Primary Examiner*—Shailendra Kumar
(74) *Attorney, Agent, or Firm*—Lahive & Cockfield, LLP; Elizabeth A. Hanley, Esq.; Jeanne M. DiGiorgio, Esq.

(57) ABSTRACT

The present invention provides a method for producing amide compounds using hydroxyl nitrile compounds and microorganisms and/or enzymatically active material having cyanide-resistant nitrile hydratase activity, e.g., *Rhodococcus equi* XL-1. Furthermore, the amide compounds can be produced while the enzymatic activity of this microorganism can be stably maintained during the reaction.

7 Claims, No Drawings

METHOD FOR PRODUCING AMIDE COMPOUNDS

RELATED APPLICATIONS

This application claims priority to the Japanese Patent Application Ser. No. 2001-182545 JP filed on Jun. 15, 2001, the entire contents of which is hereby expressly incorporated herein by reference.

FIELD OF INVENTION

The present invention relates to a method for producing amide compounds from nitrile compounds using a novel nitrile hydratase, which is highly resistant to cyanide.

BACKGROUND OF THE INVENTION

With respect to the production of α-hydroxyamide by microorganisms, method for producing corresponding amides from lactonitrile, hydroxyacetonitrile, α-hydroxy methylthiobutyronitrile, and such, using microorganisms belonging to the genus *Bacillus, Bacteridium, Micrococcus,* or *Brevibacterium* (see Examined Published Japanese Patent Application No. (JP-B) Sho 62-21519) are known in the art. In addition, method for producing mandelamide from cyanohydrin (see Unexamined Published Japanese Patent Application No. (JP-A) Hei 4-222591; JP-A Hei 8-89267) is also known in the art.

However, enzymes having nitrile hydratase activity, which possess the ability of converting nitrile compounds to amide compounds, have a problem to readily lose their enzymatic activities due to the presence of nitrile compounds or amide compounds that are the starting materials or the products, respectively. If the concentration of nitrile compound is raised in order to increase the rate of amidation within a reaction, the nitrile hydratase is readily inactivated in a short period of time, and thus it is hard to obtain amide compounds as the reaction product in a desired period of time. Furthermore, the nitrile hydratase is also readily inactivated by amide compounds, i.e. the products, and thus it is difficult to obtain amide compounds with a high concentration.

Furthermore, in varying degree depending on the type of compound, α-hydroxynitrile has been known to get partially decomposed to the corresponding aldehyde and hydrocyanic acid in a polar solvent (see V. Okano et al., J. Am. Chem. Soc., Vol. 98, 4201 (1976)). In general, aldehydes have the characteristic to bind to proteins to inactivate the enzymatic activity (see Chemical Modification of Proteins, G. E. Means et al., Holden-Day, 125(1971)). Further, like aldehyde, hydrocyanic acid (cyanide) has also an inhibitorily effect on many enzymes. Thus, aldehyde and cyanide produced from of α-hydroxynitrile as the starting material has been the cause of decreased enzymatic activity. Due to the inactivation of the enzyme in a short period of time in the enzymatic hydration or hydrolysis of α-hydroxynitrile, it has been difficult to obtain a high concentration of α-hydroxyamide with high productivity.

To prevent the decrease in the enzymatic activity, various methods for increasing the enzymatic activity or for suppressing the decrease of enzymatic activity (inactivation) have been tested. Such attempts, for example, include:

Carrying out the reaction at a lower temperature ranging from the freezing point to 15° C. (JP-B Sho 56-38118);

continuously supplying the substrate with a lower concentration from multiple supply ports (JP-B Sho 57-1234);

treating the microorganism or processed product thereof with an organic solvent (JP-A Hei 5-308980);

carrying out the reaction in the presence of higher unsaturated fatty acid (JP-A Hei 7-265090);

crosslinking the cells of microorganism with glutaraldehyde and such (JP-A Hei 7-265091; and JP-A Hei 8-154691);

lowering the concentration of hydrocyanic acid contaminated in the nitrile compound by a chemical method, and then acting the nitrile hydratase with the nitrile compound (see JP-A Hei 11-123098);

stabilizing the enzymatic activity for a long period of time by the presence of sulfite ion, acid sulfite ion or dithionite ion (see JP-A Hei 8-89267); and adding aldehyde (see JP-A Hei 4-222591).

None of these methods were sufficient enough for industrial applications. Although some of the methods were effective, there was room for economical or practical improvement. For example, the above-mentioned method of adding aldehyde requires a large quantity of aldehyde, which is 1 to 5 times molar excess to the cyanohydrin (i.e. the starting material), and thus was far from providing an economical solution. Similarly, the method wherein sulfite ion, acid sulfite ion or dithionite ion are added requires equivalent or larger amounts of ions to the starting material, and thus was not practical.

SUMMARY OF THE INVENTION

An objective of the present invention is to provide a method for producing amide compounds using nitrile hydratase that are highly resistant to cyanide and have a nitrile hydration activity. Another objective of the present invention is to provide a method for producing amide compounds using a stable nitrile hydratase that maintains the enzymatic activity at a high level for a long period. Yet another objective of the present invention is to provide a method for producing amide compounds using nitrile hydratase that can use 2-hydroxy-4-methylthiobutyronitrile as a substrate.

The present inventors strenuously studied to achieve the above-mentioned objectives, and eventually discovered a microorganism that contains a nitrile hydratase exhibiting very high nitrile hydration activity and very highly resistance to cyanide. Then, the inventors examined whether the above-mentioned objectives can be achieved by using the microorganism for the method for producing amide compounds, and completed the present invention.

Specifically, the present invention provides a method for producing amide using the cyanide-resistant nitrile hydratase as follows

[1] A method for producing amide compounds comprising the steps of:

(1) contacting a nitrile compound with a microorganism and/or enzymatically active material comprising processed product of the microorganism that has a nitrile hydratase activity, and (2) recovering produced amide compounds, wherein the residual enzymatic activity of the enzymatically active material after being treated in the presence of 20 mM cyanide ion at 20° C. for 30 minutes is at least 10% or higher of that of the material that is treated in the absence of the cyanide ion at 20° C. for 30 minutes;

[2] the method for producing amide compounds according to [1], wherein the processed product is a cell lysate or cell extract from the microorganism;

[3] the method for producing amide compounds according to [1], wherein the residual enzymatic activity of the enzymatically active material after being treated in the presence of 20 mM cyanide ion at 20° C. for 30 minutes is at least 50% or higher of that of the material that is treated in the absence of the cyanide ion at 20° C. for 30 minutes;

[4] the method for producing amide compounds according to [3], wherein the microorganism belongs to the genus *Rhodococcus*;

[5] the method for producing amide compounds according to [4], wherein the microorganism is *Rhodococcus equi*;

[6] the method for producing amide compounds according to [1], wherein the nitrile compound is α-hydroxynitrile compound and the amide compound is α-hydroxyamide;

[7] the method for producing amide compounds according to [6], wherein the α-hydroxynitrile compound is a compound represented by formula (1):

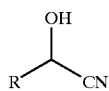

(1)

and the product is the α-hydroxyamide represented by formula (3):

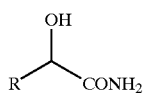

(3)

(wherein R represents a substituted or unsubstituted alkyl group, substituted or unsubstituted alkenyl group, substituted or unsubstituted cycloalkyl group, substituted or unsubstituted alkoxy group, substituted or unsubstituted aryl group, substituted or unsubstituted aryloxy group, and substituted or unsubstituted saturated or unsaturated heterocyclic group);

[8] the method for producing amide compounds according to [7], comprising the step of producing the compound represented by the formula (1) in a mixture comprising hydrocyanic acid and the aldehyde represented by formula (2):

R—CHO  (2)

(wherein R represents a substituted or unsubstituted alkyl group, substituted or unsubstituted alkenyl group, substituted or unsubstituted cycloalkyl group, substituted or unsubstituted alkoxy group, substituted or unsubstituted aryl group, substituted or unsubstituted aryloxy group, and substituted or unsubstituted saturated or unsaturated heterocyclic group); and

[9] the method for producing amide compounds according to [8], wherein the concentration of the hydrocyanic acid ranges from 0.1 mM to 20 mM in the reaction solution.

DETAILED DESCRIPTION OF THE INVENTION

A "nitrile hydratase activity" herein refers to an activity acting on the nitrile group of a nitrile compound to hydrate the nitrile group to a amide group. Preferably, an enzyme acting on the compound of formula (1) to produce the amide compound of formula (3) is designated as "nitrile hydratase". Formula (1):

Formula (3):

wherein R represents a substituted or unsubstituted alkyl group, substituted or unsubstituted alkenyl group, substituted or unsubstituted cycloalkyl group, substituted or unsubstituted alkoxy group, substituted or unsubstituted aryl group, substituted or unsubstituted aryloxy group, and substituted or unsubstituted saturated or unsaturated heterocyclic group.

According to the present invention, a nitrile hydratase activity preferably refers to the enzymatic activity that acts on 2-hydroxy-4-methylthiobutyronitrile to produce 2-hydroxy-4-methylthiobutyroamide.

The nitrile hydratase activity of the present invention can be determined as follows. First, an enzyme sample is added to a 0.1 M potassium phosphate buffer (pH 6.5) containing 10% v/v 2-hydroxy-4-methylthiobutyronitrile (HMBN) as the substrate. Instead of the enzyme sample, cells of microorganisms and crude enzymes can be also used. After the addition of the enzyme, the solution is incubated at 20° C. for 15 minutes. The reaction solution is then added to an excess volume of 0.1% (v/v) phosphate solution, and the mixture is shaken vigorously to quench the reaction. The reaction product can be analyzed by HPLC.

According to this assay method, 1 U of nitrile hydratase was defined as the amount of enzyme producing 1 μmol nicotinamide at 20° C. for 1 minute in a reaction solution with a standard composition; 1 U was defined as the amount of enzyme producing 1 μmol HMBAm at 20° C. for 1 minute in a reaction solution with a standard composition.

Specifically, for example, the enzymatic activity can be assayed by a procedure as described in Examples. Further, protein quantification is carried out by the dye-binding method using a protein assay kit from Bio-Rad.

On the other hand, as used herein, the term "cyanide resistance" indicates that the residual nitrile hydratase activity of the enzyme is 10% or higher of the original level, preferably 50% or higher of the original level after being treated in the presence of 20 mM cyanide ion at 20° C. for 30 minutes. The present inventors have previously isolated a nitrile hydratase from a microorganism belonging to the genus *Rhodococcus*; which enzymatic activity is 10% or higher of the original level even after being treated in the presence of 5 mM cyanide ion at 20° C. for 30 minutes. This enzyme, like the enzyme of the present invention, has suitable characteristics for the production of amide compounds. However, the nitrile hydratase of the present invention has novelty to the previously known enzyme due to the markedly high cyanide resistance.

The type of cyanide-resistant microorganism is not limited so long as the nitrile hydratase derived from the microorganism has an residual activity that is 10% or higher, preferably 50% or higher, more preferably 80% or higher of the original activity level even after being treated in the presence of 20 mM cyanide ion at 20° C. for 30 minutes.

Alternatively, enzymatically active materials can be also used so long as the nitrile hydratase activity thereof after being incubated under the same condition in the presence of cyanide is 10% or higher, preferably 15% or higher of the activity wherein the extract has been incubated in the absence of cyanide.

A preferred microorganism of the present invention is for example, a microorganism that meets the above-mentioned requirements and that is selected from microorganisms belonging to the genus *Rhodococcus*. More specifically, *Rhodococcus equi* XL-1 is a preferred microorganism for producing amide compounds according to the present invention. *Rhodococcus equi* XL-1 has been deposited as follows:

(a) Name and address of depositary
    Name: Institute for Fermentation, Osaka (IFO)
    Address: 17-85, Juso-honmachi 2-chome, Yodogawa-ku, Osaka, Japan (Zip code 532-8686)
(b) Date of deposition: May 31, 2002
(c) Accession number: IFO 16802

The above-mentioned microorganism having the cyanide-resistant nitrile hydratase activity and/or enzymatically active material comprising processed product thereof are useful in producing amide compounds. More specifically, the present invention provides a method for producing amides, comprising the steps of: (1) contacting a nitrile compound with the above-mentioned microorganism having the cyanide-resistant nitrile hydratase activity and/or enzymatically active material comprising processed products thereof, and (2) recovering the amide produced.

According to the present invention, processed products of microorganisms specifically includes microorganisms whose cell membrane permeability has been modified by the treatment with a detergent or organic solvent, such as toluene; cell-free extracts obtained by lysing cells by the treatment with glass beads or enzyme; materials partially purified from the extract; and so on. Whereas, the processed products of enzyme includes enzymes linked with insoluble carriers or with aqueous carrier molecules; immobilized enzyme molecules prepared by entrapping; and so on.

The type of nitrile compound to be used in the method for producing amides using any one of enzymatically active materials, which is selected from the group consisting of the microorganisms containing the activity of cyanide-resistant nitrile hydratase of the present invention, or processed products thereof, are not limited in any way. For example, following nitrile compounds can be used in the production method of the present invention.

Saturated Mononitriles:
acetonitrile, propionitrile, butyronitrile, isobutyronitrile, valeronitrile, isovaleronitrile, capronitrile, etc.

Saturated Dinitriles:
malonitrile, succinonitrile, glutarnitrile, adiponitrile, etc.

α-Aminonitriles:
α-aminopropionitrile, α-aminomethylthiobutyronitrile, α-aminobutyronitrile, aminoacetonitrile, etc.

Nitriles Having Carboxyl Groups:
cyanoacetic acid, etc.

β-Aminonitriles:
amino-3-propionitrile, etc.

Unsaturated Nitriles:
acrylonitrile, methacrylonitrile, allyl cyanide, crotononitrile, etc.

Aromatic Nitriles:
benzonitrile; o-, m-, and p-chlorobenzonitrile; o-, m-, and p-fluorobenzonitrile; o-, m-, and p-nitrobenzonitrile; p-aminobenzonitrile; 4-cyanophenol; o-, m-, and p-tolunitrile; 2,4-dichlorobenzonitrile; 2,6-dichlorobenzonitrile; 2,6-difluorobenzonitrile; anisonitrile; α-naphthonitrile; α-naphthonitrile; phthalonitrile; isophthalonitrile; terephthalonitrile; benzyl cyanide; phenylacetonitrile; etc.

α-hydroxynitriles.

According to the present invention, particularly preferable nitrile compounds include α-hydroxynitrile compound. In the amide-producing method of the present invention, the type of α-hydroxynitrile compound is not limited in any way. More specifically, for example, compounds represented by the above formula (1) can be used.

Wherein R in the formula represents a substituted or unsubstituted alkyl group, substituted or unsubstituted alkenyl group, substituted or unsubstituted cycloalkyl group, substituted or unsubstituted alkoxy group, substituted or unsubstituted aryl group, substituted or unsubstituted aryloxy group, and substituted or unsubstituted saturated or unsaturated heterocyclic group. α-hydroxyamide can be produced from α-hydroxynitrile compounds.

The heterocyclic group includes the groups having at least one of the atoms selected from the group of nitrogen, oxygen, and sulfur as the heteroatom. Further, the substituent includes, for example, alkyl group; alkoxy group; acyl group; aryl group; aryloxy group; halogens, such as chloride and bromide; hydroxy group; amino group; nitro group; thiol group; and such.

Specifically, for example, the following compounds or substituted products thereof can be used. As used herein, the term "substituted product" refers to compounds having substituents as those exemplified above.

Lactonitrile;
α-hydroxy-n-propionitrile;
α-hydroxy-n-butyronitrile;
α-hydroxy-isobutyronitrile;
α-hydroxy-n-hexyronitrile;
α-hydroxy-n-heptyronitrile;
α-hydroxy-n-octyronitrile;
α,γ-dihydroxy-β,β-dimethylbutyronitrile;
acroleincyanohydrin;
methacrylaldehyde cyanohydrin;
3-chlorolactonitrile;
4-methylthio-α-hydroxybutyronitrile; and
α-hydroxy-α-phenylpropionyl.

Further, substrate compounds having aromatic ring and heterocycle are exemplified by compounds and substituted products thereof as follows:

Mandelonitrile;
2-thiophenecarboxyaldehyde cyanohydrin;
2-pyridinecarboxyaldehyde cyanohydrin;
2-pyrrolecarboxyaldehyde cyanohydrin;
2-furaldehyde cyanohydrin; and
2-naphthylaldehyde cyanohydrin.

Many of the nitrile compounds represented by the α-hydroxynitrile compound of formula (1) are decomposed into aldehyde and hydrocyanic acid in a polar solvent. For example, the α-hydroxynitrile compound of formula (1) is converted to the aldehyde of the above formula (2) and hydrocyanic acid. Since a state of equilibrium is established among these compounds, the consumption of α-hydroxynitrile compound by enzyme reaction shifts the equilibrium toward the α-hydroxynitrile compound.

On the other hand, cyanides and aldehydes derived from hydrocyanic acid generally damage enzyme polypeptides. Accordingly, previously known nitrile hydratases cannot hydrate sufficient amounts of α-hydroxynitrile compound due to the decrease of the enzymatic activity, and thus do not provide enough yields of product. However, the nitrile hydratase of the present invention retains the enzymatic activity even in the presence of cyanide or aldehyde. Thus, the enzyme can utilize nitrile compounds generated from aldehydes and hydrocyanic acids as the substrate. Accordingly, according to the method for producing α-hydroxyamide of the present invention, the compound of formula (1) can be supplied from the aldehyde compound represented by the above formula (2) and hydrocyanic acid.

According to the present invention, hydration or hydrolysis of a nitrile compound can be achieved by contacting the enzymatically active material of the present invention with a substrate compound or a mixture of aldehyde, represented by formula (2), and hydrocyanic acid, which can be converted to a substrate compound, in an aqueous solvent, such as water or buffer.

As used herein, the term "hydration" refers to a reaction wherein water molecules are added to the nitrile group. In contrast to "hydration", the term "hydrolysis" refers to a reaction wherein the substituent bound to the nitrile group of a compound is cleaved off by hydrolysis. Both reactions are included in the amide-producing method of the present invention.

The concentration of substrate compounds in the reaction solution is not limited. In order to prevent the inhibition of enzymatic activity by the substrate compound, the concentration can be generally in the case of α-hydroxynitrile, for example, 0.1 to 10 w/w %, preferably 0.2 to 5.0 w/w/ %. The substrate can be added once at the start of the reaction. However, it is preferable to add the substrate continuously or discontinuously to prevent the substrate concentration from getting too high.

When the solubility of nitrile compound as the substrate in the aqueous solvent is too low, a detergent can be added to the reaction solution. As the detergent, 0.1 to 5.0 w/w % Triton X-100 or Tween 60 can be used. To increase the substrate solubility, a mixed solvent containing organic solvent can be effectively used. Specifically, for example, the reaction efficiency can be improved by adding methanol, ethanol, dimethylsulfoxide, and such. Alternatively, the reaction of the present invention can be achieved in an organic solvent insoluble with water or two-phase system consisting of aqueous solvent and organic solvent insoluble with water. The organic solvents immiscible with water to be used in the invention include, for example, ethyl acetate, butyl acetate, toluene, chloroform, n-hexane, cyclohexane, octane, 1-octanol, etc.

When the substrate concentration falls within the range as described above, an efficient enzymatic reaction can be achieved by a microorganism having the cyanide resistant-nitrile hydratase activity and/or enzymatically active material comprising processed products of the microorganism of the present invention at an enzyme concentration, for example, of 1 mU/mL to 100 U/mL, preferably 100 mU/mL or higher.

Further, when cells of the microorganisms are used as the enzymatically active material, the amount of microorganisms to be used in relation to the substrate preferably ranges from 0.01 to 5.0 w/w % as dry cells. The enzymatically active material, such as enzyme and cells, can be contacted with the substrate by dissolving or dispersing them in a reaction solution. Alternatively, it is possible to use the enzymatically active material by immobilizing them according to the techniques of chemical linking or entrapment. Moreover, the reaction can be carried out in a state wherein the substrate solution and the enzymatically active material are separated by a porous membrane, that allows the permeation of substrate but restricts the permeation of enzyme molecules and cells.

The reaction can be carried out typically at a temperature ranging from the freezing point to 50° C., preferably at 10 to 30° C., for 0.1 to 100 hours. The pH of the reaction solution is not limited so long as the enzymatic activity is maintained.

Thus, a nitrile compound is converted to the corresponding amide compound by the hydration or hydrolysis action of the microorganism, and accumulates in the reaction solution. The produced amide can be recovered and purified from the reaction solution by appropriate methods. Specifically, for example, the amide can be recovered and purified by the combined use of typical methods, such as ultrafiltration, concentration, column chromatography, extraction, treatment with activated charcoal, distillation, etc.

The present invention provides a method for producing amide compounds using a nitrile hydratase highly resistant to cyanide and producing 2-hydroxy-4-methylthiobutyroamide from 2-hydroxy-4-methylthiobutyronitrile as a substrate. 2-hydroxy-4-methylthiobutyroamide is a useful compound as a feed additive (a methionine substitute).

Further, the nitrile hydratase highly resistant to cyanide according to the present invention retains the high enzymatic activity in the presence of cyanide or aldehyde. In a polar solvent, the substrate compound, α-hydroxynitrile, is decomposed to hydrocyanic acid and aldehyde. Hydrocyanic acid is converted to cyanide, which often reduces the enzymatic activity. Aldehyde also damages the protein and reduces the enzymatic activity. One of the reasons why known nitrile hydratases were not industrially applicable was that these cyanide and aldehyde reduce the enzymatic activity.

By the method for producing amide compounds using a nitrile hydratase highly resistant to cyanide according to the present invention, the enzymatic activity can be retained even in the presence of cyanide or aldehyde, and amide compounds can be efficiently produced using, as the substrate, α-hydroxynitrile generated from aldehyde and hydrocyanic acid. Thus, the method using the nitrile hydratase highly resistant to cyanide of the present invention is a useful method for producing amide compounds using α-hydroxynitrile as a starting material.

The present invention is illustrated in detail below with reference to examples, but is not to be construed as being limited thereto.

Exemplification

EXAMPLE 1

Method for Determining Enzymatic Activity

A standard method for determining the nitrile hydratase activity used in the following Examples was as follows. A standard composition of the reaction solution for the enzyme reaction is shown in Tables 1 and 2. The enzyme reaction is initiated by adding 3-cyanopyridine or 2-hydroxy-4-methylthiobutyronitrile (HMBN) as the substrate compound. In the case of 3-cyanopyridine, incubation was continued at 20° C. for 10 minutes; whereas it was conducted at 20° C. for 15 minutes for HMBN. When 3-cyanopyridine was used in the reaction, 0.1 ml of 2 N hydrochloric acid was added to the reaction and the mixture was shaken vigorously to stop the reaction; when HMBN was used in the reaction, 0.1 ml of the reaction solution was added to 0.9 ml of 0.1% (v/v) phosphoric acid and the mixture was shaken vigorously to stop the reaction. The reaction solution was analyzed by HPLC.

TABLE 1

| | |
|---|---|
| 10% (v/v) HMBN in 0.1 M KPB (pH 6.5) | 0.36 ml |
| 0.1 M KPB (pH 6.5) | 0.64 ml |
| Enzyme solution | 0.10 ml |
| 0.85% (w/v) NaCl aq | 0.90 ml |
| Total volume | 2.00 ml |

The reaction was conaducted as follows:
1) 10% (v/v) HMBN was added to initiate the reaction;
2) the mixture was incubated with shaking at 20° C. for 10 minutes;
3) 0. 1% (v/v) $H_3PO_4$ was added to stop the reaction;
4) the reacted solution was centrifugated; and
5) was subjected to HPLC analysis.

TABLE 2

| | |
|---|---|
| 0.3 M 3-cyanopyridine | 0.50 ml |
| 0.1 M KPB (pH 7.0) | 0.50 ml |
| Enzyme solution | 0.10 ml |
| 0.85% (w/v) NaCl aq | 0.90 ml |
| Total volume | 2.00 ml |

The reaction was conducted as follows:
1) 0.3 M 3-cyanopyridine was added to initiate the reaction;
2) the mixture was incubated with shaking at 20° C. for 3 minutes;
3) 2 N HCl was added to stop the reaction;
4) the reacted solution was centrifuged; and
5) was subjected to HPLC analysis.

The conditions used in the HPLC analysis of the reaction solution was as follows:
The conditions used in the HPLC analysis for HMBN was as follows:

| | |
|---|---|
| Column: | Spherisorb S5ODS2 (4.6 × 150 nm); |
| Mobile phase: | 0.1% (v/v) phosphoric acid/acetonitrile = 9/1; |
| Flow rate: | 1.0 ml/min.; |
| Detection: | UV 210 nm; |
| Column temperature: | 40° C. |

HPLC Analysis for Determining Enzymatic Activity:

The generated nicotinamide or HMBAm was quantified by HPLC, and the nitrile hydratase activity was calculated. The conditions of HPLC assay for HMBAm were the same as that for HMBN. 1 U was defined as the enzyme quantity producing 1 μmol nicotinamide from a standard composition of the reaction solution at 20° C. for 1 minute; or 1 U was defined as the enzyme quantity producing 1 μmol HMBAm from a standard composition of the reaction solution at 20° C. for 1 minute.

EXAMPLE 2

Culture Conditions 5 ml pre-culture medium of the following composition was aliquoted into each test tube (25×200 mm); a silicone plug was placed in the tube, followed by sterilization by autoclaving. After the tube was cooled, a bacterial strain was inoculated with a platinum loop, and then cultured with shaking at 28° C. for two days.

Pre-Culture Medium (pH 7.0):

| | |
|---|---|
| Polypeptone | 5.0 g |
| Meat extract | 5.0 g |
| NaCl | 2.0 g |
| Yeast extract | 0.5 g, and |
| Distilled water | 1.0 L. |

Then, the pre-culture was transferred into 20-ml main-culture medium autoclaved in a 500-ml Sakaguchi flask. In the main culture, 0.75% (v/v) acetonitrile was added after 24-hour culture, and then the incubation was continued with shaking at 33° C. for two days.

Main-Culture Medium (pH 7.0):

| | |
|---|---|
| Acetamide | 7.5 g |
| Glucose | 10.0 g |
| C.S.L. | 10.0 g |
| Yeast extract | 1.0 g |
| $MgSO_4 7H_2O$ | 0.5 g |
| $K_2HPO_4$ | 1.0 g |
| $CoCl_2 6H_2O$ | 20.0 mg, and |
| Distilled water | 1.0 L. |

EXAMPLE 3

Isolation and Identification of Microorganisms

XL-1 strain was selected as a strain with particularly high ability of decomposing nitrites from nitrile-decomposing bacteria obtained from soil collected in the campus of Gifu University by enrichment culture with a medium containing various nitrites. Since this strain had the following microbiological characteristics, according to "Bergey's Manual of Determinative Bacteriology (ninth edition, 1994)", it was identified as *Rhodococcus equi,* which is a strain belonging to the genus *Rhodococcus.*

1. Morphological Characteristics
   (1) Cellular polymorphism: life cycle comprising bacillar and coccal forms
   (2) Gram staining: +
   (3) Spore formation: −
   (4) Motility: −
   (5) Colony appearance: round-shaped, smooth-edged, less convex, glossy, pink.
2. Characteristics Involved in Culture
   (1) Broth liquid culture: suspension
   (2) Litmus milk: unchanged.
3. Physiological Characteristics
   (1) Denitrification reaction: −
   (2) MR test: −
   (3) VP test: −
   (4) Hydrogen sulfide production: −
   (5) Starch hydrolysis: −
   (6) Citrate test: Koser+Christensen+w
   (7) Inorganic nitrogen source test: $NaNO_3$+$(NH_4)_2SO_4$+
   (8) Growth temperature: 10° C.+w 40° C.+45° C.−
   (9) Anaerobic growth: −
   (10) Catalase: +
   (11) Oxidase: −
   (12) O/F test: −

Further, DNA was extracted from cells of the strain, and the nucleotides of the 16S rDNA corresponding to the 16S rRNA were amplified by PCR. The segment of the first 500 nucleotides was compared for homology with various known strains belonging to the genus *Rhodococcus* in the MicroSeq database. The sequence showed 100% homology to that of *Rhodococcus equi*, and thus the strain was concluded to be *Rhodococcus equi*.

EXAMPLE 4

The Effect of Cyanide Ion (1)

The effect of cyanide ion on *Rhodococcus erythropolis* IFO 12539, 12540, 12567, 12320, ATCC11048, *Rhodococcus rhodochous* ATCC33278, and *Rhodococcus equi* XL-1 was studied using respective bacterial cells with 2.4 U, 5.8 U, 5.6 U, 6.2 U, 2.8 U, 17.7 U, and 12.8 U nitrile hydratase activity per 1 ml. With the following standard composition of reaction solution, 0 mM to 20 mM cyanide ion (KCN) was added to the reaction system. After the solution was incubated in the absence of the substrate (i.e., 3-cyanopyridine) at 20° C. for 30 minutes, the enzyme reaction was started with the addition of the substrate. After the enzyme reaction at 20° C. for 10 minutes, 0.1 ml of 2 N hydrochloric acid was added thereto and the mixture was vigorously shaken to stop the reaction. The reaction solution was analyzed by HPLC as described in Example 1.
Standard Reaction Solution:

| | |
|---|---|
| 0.5 M 3-cyanopyridine | 0.5 ml |
| 0.1 M phosphate buffer (pH 7.5) | 0.25 ml |
| Enzyme solution | 0.1 ml |
| Total volume | 1.0 ml |

As seen in Table 3, after the incubation in the presence of 20 mM cyanide ion, the residual activities of *Rhodococcus erythropolis* IFO 12539, 12540, 12567, 12320, ATCC11048, and *Rhodococcus rhodochous* ATCC33278 were 4%, 13%, 11%, 0%, 7%, and 11%, respectively. On the other hand, the residual activity of *Rhodococcus equi* XL-1 was 89%.

TABLE 3

| Strain name | 0 mM | 1 mM | 5 mM | 10 mM | 15 mM | 20 mM |
|---|---|---|---|---|---|---|
| Rhodococcus equiXL-1 | 100 | 100 | 100 | 98 | 94 | 89 |
| Rhodococcus erythropolis IFO 12539 | 100 | 51 | 13 | 9 | 5 | 4 |
| Rhodococcus erythropolis IFO 12540 | 100 | 92 | 79 | 39 | 16 | 13 |
| Rhodococcus erythropolis IFO 12567 | 100 | 82 | 62 | 47 | 16 | 11 |
| Rhodococcus erythropolis IFO 12320 | 100 | 21 | 2 | 1 | 0 | 0 |
| Rhodococcus erythropolis ATCC11048, | 100 | 54 | 30 | 18 | 10 | 7 |
| Rhodococcus rhodochous ATCC33278 | 100 | 61 | 36 | 42 | 14 | 11 |

EXAMPLE 5

The Effect of Cyanide Ion (2)

The effect of cyanide ion on the nitrile hydratase of the present invention derived from *Rhodococcus equi* XL-1, and known nitrile hydratase derived from *Rhodococcus rhodochous* J1 (Biochimica et Biophysica Acta. 1129(1991): 23–33) was studied using bacterial cell extracts thereof. With the following standard composition of reaction solution, 0 mM to 20 mM cyanide ion (KCN) was added to the reaction system. After the reaction solution was incubated in the absence of substrate (i.e., 3-cyanopyridine) at 20° C. for 30 minutes, the substrate was added thereto to start the enzyme reaction. After the enzyme reaction at 20° C. for 10 minutes, 0.1 ml of 2 N hydrochloric acid was added thereto and the mixture was shaken vigorously to stop the reaction. The reaction solution was analyzed by HPLC according to the same method as described in Example 1.
Standard Reaction Solution:

| | |
|---|---|
| 0.5 M 3-cyanopyridine | 0.5 ml |
| 0.1 M phosphate buffer (Ph 7.5) | 0.25 ml |
| Enzyme solution | 0.1 ml |
| Total volume | 1.0 ml |

The reaction was carried out with 60 U/ml nitrile hydratase of *Rhodococcus equi* XL-1 or 61 U/ml nitrile hydratase of *Rhodococcus rhodochous* J1. As seen in Table 4, the nitrile hydratase of *Rhodococcus rhodochous* J1 was completely inhibited in the presence of 20 mM cyanide ion, but the residual activity of nitrile hydratase of *Rhodococcus equi* XL-1 was 20% in the presence of 20 mM cyanide ion. A markedly higher degree of enzyme inactivation due to cyanide was seen with the bacterial extract than with the living bacterial cells. However, the nitrile hydratase in the cell extract of *Rhodococcus equi* XL-1 can retain its enzymatic activity even in the presence of cyanide.

TABLE 4

| KCN (mM) | Rhodococcus equiXL-1 | Rhodococcus rhodochous J 1 |
|---|---|---|
| 0 | 100 | 100 |
| 1 | 93 | 0 |
| 5 | 68 | 0 |
| 10 | 47 | 0 |
| 15 | 30 | 0 |
| 20 | 20 | 0 |

EXAMPLE 6

Production of 2-hydroxy-4-methylthiobutyric Acid Amide (HMBAm) from 2-hydroxy-4-methylthiobutyronitrile Using Bacterial Cells (A) Culture
*Rhodococcus equi* XL-1 was cultured under the following condition.
(1) Medium Composition (Unit: wt %)

| | |
|---|---|
| Ethanol | 2.0% |
| C.S.L. | 1.0% |
| Yeast extract | 0.1% |
| Crotonamide | 0.4% |
| Magnesium sulfate heptahydrate | 0.05% |
| Potassium phosphate monobasic | 0.2% |
| pH 7.2 | |

(2) Culture Condition
Bacterial cells were taken with a platinum loop from slant medium, and inoculated into 40 ml of the above-mentioned liquid medium autoclaved in a Sakaguchi flask. The cells were incubated with shaking under aerobic condition at 28° C. for 3 days.

(B) Reaction

After culture, the bacterial cells were harvested from the liquid medium by centrifugation. The wet bacterial cells (1 g) was suspended in 25 g of a reaction solution (0.05 M phosphate buffer (pH 6.5), 2-hydroxy-4-methylthiobutyronitrile (0.2 wt %), and NaCl (0.34 wt %)) in a 200-ml flask. The solution in the flask was incubated at 30° C. for 43 hours with stirring; and 2-hydroxy-4-methylthiobutyronitrile was added during the reaction. When the initial HMBN concentration was 537 mM, the concentration of cyanide ion in the reaction solution was 2.33 mM. After the reaction, HMBAm concentration in the reaction solution was 75 g/L. HMBAm was quantified by high-performance liquid chromatography (column: Sperisorb S50DS2 (4.6×150 mm); mobile phase: 0.1% (V/V) phosphoric acid (pH 4.6):acetonitrile =9: 1; flow rate: 1.0 ml/min.; detection: 210 nm; column temperature: 40° C.).

The reaction solution was extracted with an equal volume of methylethylketone, and then desolvated. The recovered product was identified as 2-hydroxy-4-methylthiobutyric acid amide by NMR analysis.

The contents of all references, pending patent application and published patent applications, cited throughout this application, including those referenced in the background section, are hereby incorporated by reference.

Equivalents

Those skilled in the art will recognize, or be able to ascertain using no more than routine experimentation, many equivalents to the specific embodiments of the invention described herein. Such equivalents are intended to be encompassed by the following claims.

What is claimed is:

1. A method for producing amide compounds comprising the steps of:
   (i) contacting a nitrile compound with *Rhodococcus equi* XL-l and/or enzymatically active material comprising processed product of the microorganism that has a nitrile hydratase activity, and
   (ii) recovering produced amide compounds, wherein the residual enzymatic activity of the enzymatically active material after being treated in the presence of 20 mM cyanide ion at 20° C. for 30 minutes is at least 10% or higher of that of the material that is treated in the absence of the cyanide ion at 20° C. for 30 minutes.

2. The method for producing amide compounds according to claim 1, wherein the processed product is a cell lysate or cell extract from the microorganism.

3. The method for producing amide compounds according to claim 1, wherein the residual enzymatic activity of the enzymatically active material after being treated in the presence of 20 mM cyanide ion at 20° C. for 30 minutes is at least 50% or higher of that of the material that is treated in the absence of the cyanide ion at 20° C. for 30 minutes.

4. The method for producing amide compounds according to claim 1, wherein the nitrile compound is α-hydroxynitrile compound and the amide compound is α-hydroxyamide.

5. The method for producing amide compounds according to claim 4, wherein the α-hydroxynitrile compound is a compound represented by formula (1):

and the product is the α-hydroxyamide represented by formula (3):

(wherein R represents a substituted or unsubstituted alkyl group, substituted or unsubstituted alkenyl group, substituted or unsubstituted cycloalkyl group, substituted or unsubstituted alkoxy group, substituted or unsubstituted aryl group, substituted or unsubstituted aryloxy group, and substituted or unsubstituted saturated or unsaturated heterocyclic group).

6. The method for producing amide compounds according to claim 5, comprising the step of:
   (i) producing the compound represented by the formula (1) in a mixture comprising hydrocyanic acid; and

(ii) the aldehyde represented by formula (2):
wherein R represents a substituted or unsubstituted alkyl group, substituted or unsubstituted alkenyl group, substituted or unsubstituted cycloalkyl group, substituted or unsubstituted alkoxy group, substituted or unsubstituted aryl group, substituted or unsubstituted aryloxy group, and substituted or unsubstituted saturated or unsaturated heterocyclic group.

7. The method for producing amide compounds according to claim 6, wherein the concentration of the hydrocyanic acid ranges from 0.1 mM to 20 mM in the reaction solution.

* * * * *